(12) United States Patent
McIntyre et al.

(10) Patent No.: US 9,937,347 B2
(45) Date of Patent: Apr. 10, 2018

(54) ACTIVATION MAP BASED INDIVIDUALIZED PLANNING FOR DEEP BRAIN STIMULATION

(71) Applicant: Case Western Reserve University, Cleveland, OH (US)

(72) Inventors: Cameron McIntyre, Cleveland, OH (US); Patricio Riva-Posse, Atlanta, GA (US); Ki Sueng Choi, Atlanta, GA (US); Ashutosh Chaturvedi, Cleveland, OH (US); Helen Mayberg, Atlanta, GA (US); Michele Tagliati, Pacific Palisades, CA (US); Tyler Cheung, Los Angeles, CA (US)

(73) Assignee: Case Western Reserve University, Cleveland, OH (US)

( * ) Notice: Subject to any disclaimer, the term of this patent is extended or adjusted under 35 U.S.C. 154(b) by 202 days.

(21) Appl. No.: 14/557,161

(22) Filed: Dec. 1, 2014

(65) Prior Publication Data

US 2015/0157858 A1 Jun. 11, 2015

Related U.S. Application Data

(60) Provisional application No. 61/913,349, filed on Dec. 8, 2013, provisional application No. 61/954,638, filed on Mar. 18, 2014.

(51) Int. Cl.
*A61N 1/36* (2006.01)
*A61N 1/05* (2006.01)

(52) U.S. Cl.
CPC ....... *A61N 1/3606* (2013.01); *A61N 1/36139* (2013.01); *A61N 1/0534* (2013.01); *A61N 1/36064* (2013.01); *A61N 1/36067* (2013.01); *A61N 1/36096* (2013.01)

(58) Field of Classification Search
CPC .............. A61N 1/3605; A61N 1/36082; A61N 1/36003; A61N 1/36; A61N 1/36014
USPC ...................................................... 607/45, 48
See application file for complete search history.

(56) References Cited

U.S. PATENT DOCUMENTS

2003/0073917 A1* 4/2003 Echauz ................ A61B 5/0476 600/510
2014/0296702 A1* 10/2014 Griswold ........... G01R 33/3614 600/416

* cited by examiner

*Primary Examiner* — Michael Carey
*Assistant Examiner* — Roland Dinga
(74) *Attorney, Agent, or Firm* — Eschweiler & Potashnik, LLC (57) ABSTRACT

Example apparatus and methods plan and control neuromodulation of a distributed multi-region network in a brain. A location for a deep brain stimulation (DBS) electrode that participates in activating a combination of white matter pathways associated with the network is selected. The location is selected based on a pre-implantation image of the brain and a probabilistic activation model of the network. An initial stimulation parameter for DBS to be applied through the DBS electrode is selected based on a post-implantation image of the brain and the probabilistic activation model of the network. A modified stimulation parameter for DBS being applied through the DBS electrode is selected based on the initial stimulation parameter, a local field potential measured in the distributed multi-region network in response to DBS applied using the initial stimulation parameter, the probabilistic activation model of the distributed multi-region network, and the post-implantation image of the brain.

19 Claims, 8 Drawing Sheets

ACTIVATION MAP BASED INDIVIDUALIZED PLANNING FOR DEEP BRAIN STIMULATION

CROSS REFERENCE TO RELATED APPLICATIONS

This application claims the benefit of U.S. Provisional Application 61/913,349 filed Dec. 8, 2013 and U.S. Provisional Application 61/954,638 filed Mar. 18, 2014, both of which are incorporated herein by reference.

BACKGROUND

One aspect of deep brain stimulation (DBS) that has confounded researchers is that identical anatomical placement of electrodes in different patients produces different results. Identical contact locations theoretically should produce identical or at least similar results. However, in at least DBS of the subcallosal cingulate (SCC) for treatment of treatment resistant depression (TRD), anatomically identical placements of contacts has yielded different results as detailed in provisional applications 61/913,349 and 61/954,638.

Clinical trials of DBS have demonstrated significant therapeutic benefits for the treatment of neuropsychiatric disorders. However, conventional approaches have struggled with identifying the precise therapeutic mechanisms, optimal stimulation targets, or specific axonal pathways for an individual patient. While human brains are remarkably alike at the gross anatomical level, human brains may exhibit different network connectivity between regions in response to DBS. For example, even though gross anatomy may be similar, a common anatomical location may not coincide with a hub location for various white matter bundles and thus theoretically identical DBS may produce different results.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example apparatus and methods select DBS contact locations and DBS parameters (e.g., voltage, frequency, wave type) for a specific patient based on population activation models, pre-operative medical images of the patient, patient-specific activation maps, real-time assessment of the activation achieved by a stimulation, or a desired therapeutic effect for the specific patient. The patient specific maps may be based, at least in part, on pre-operative medical imaging including, for example, diffusion tensor based magnetic resonance imaging (MRI). Example apparatus and methods may also alter DBS parameters based on measured local field potentials (LFPs) produced using DBS electrodes and DBS parameters, population activation models, pre-operative medical images of the patient, post-operative medical images of the patient that show the actual location of an implanted electrode, patient-specific activation maps, real-time assessment of the activation achieved by a stimulation, or a desired therapeutic effect for the specific patient.

Example apparatus and methods facilitate placing a DBS contact (e.g., electrode) to achieve selective activation of a combination of targeted axonal pathways to achieve a desired therapeutic effect. An example method may include performing pre-operative MRI to plan locations for one or more DBS contacts to facilitate activating the combination of targeted axonal pathways. An example method may assess a post-operative MRI to determine actual locations of the one or more DBS contacts following implantation. The example method may monitor activation resulting from stimulation. The pre-operative imaging may be evaluated in light of population based imagery.

For TRD and other conditions, electrode placement and stimulation parameters may be selected to impact critical local regions and a combination of distributed white matter tracts linking the stimulation site(s) to the target site(s). Rather than targeting a single site, a combination of pathways may be targeted. For example, for TRD, the combination of white matter pathways may include a pathway from the bilateral forceps to the medial frontal cortex, a pathway from the cingulate bundle to the cingulate cortex, and a pathway from the descending subcortical midline fibers to the subcortical nuclei. The DBS contacts may be placed and the DBS parameters may be selected to cause activation in the combination of pathways.

Unlike conventional systems and methods, electrode position or stimulation parameters are not determined solely by gross anatomy. Instead, activation volumes for electrodes that have been surgically implanted can be calculated using a combination of probabilistic tractography maps or real-time stimulation/activation analysis. Stimulation parameters can then be selected based on the post-operative images and recorded local field potentials.

Example apparatus and methods may perform patient-specific target selection and stimulation parameter selection and control based on modelled and/or measured network connectivity to modulate a distributed multi-region network in addition to local changes in SCC gray matter. Changes in brain regions remote from a stimulation site may be more important to the therapeutic effect than changes at a stimulation site.

Figure 1:
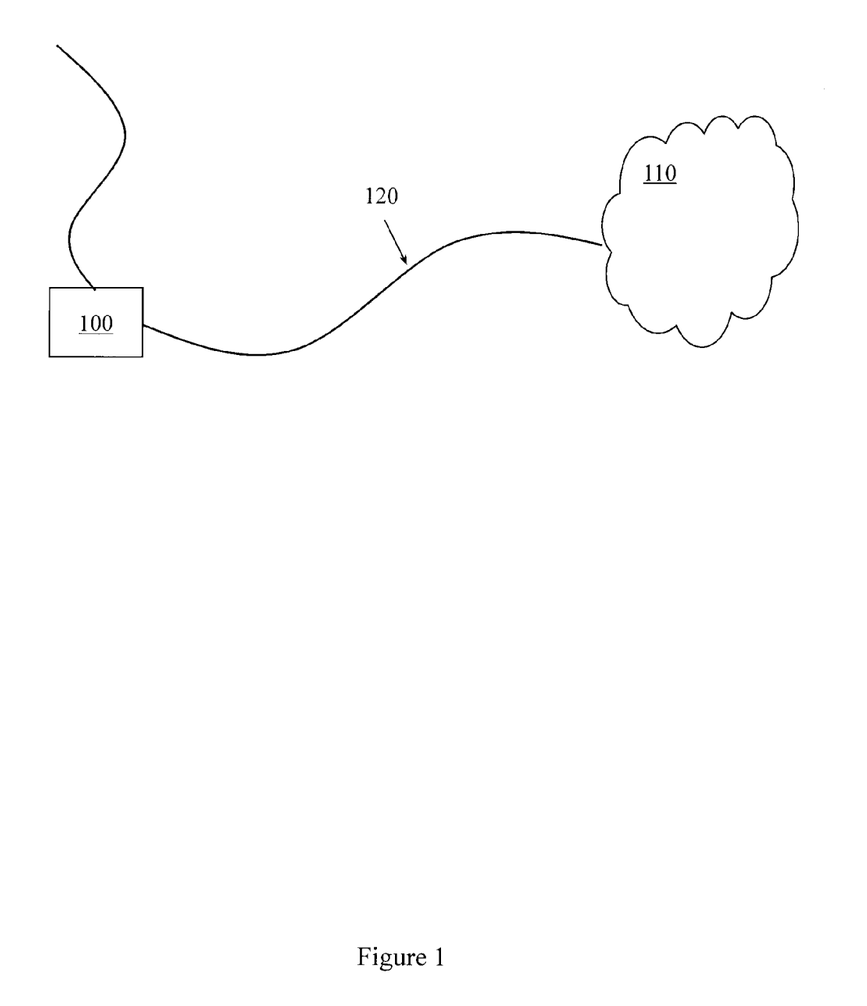
FIG. 1 illustrates an electrode connected to a target activation site via a white matter pathway.

FIG. 1 illustrates an electrode 100 connected to a target activation area 110 via a white matter pathway 120. Example apparatus and methods may use a plurality of electrodes to activate a plurality of target activation areas via a plurality of white matter pathways. For example, a first pathway may connect an electrode to the right and left medial frontal cortex via the bilateral forceps minor of the anterior corpus callosum or the medial aspect of the uncinated fasciculus. A second pathway may connect an electrode to the rostral and dorsal anterior and mid cingulate cortex via the bilateral cingulate bundle. A third pathway may connect an electrode to the subcortical nuclei via the short sub cortical descending midline fibers. The subcortical nuclei may include the nucleus accumbens, the anterior thalamus, or the caudate putomen. The short subcortical descending midline fibers may include the medial front striatal subcortical fibers.

Figure 2:
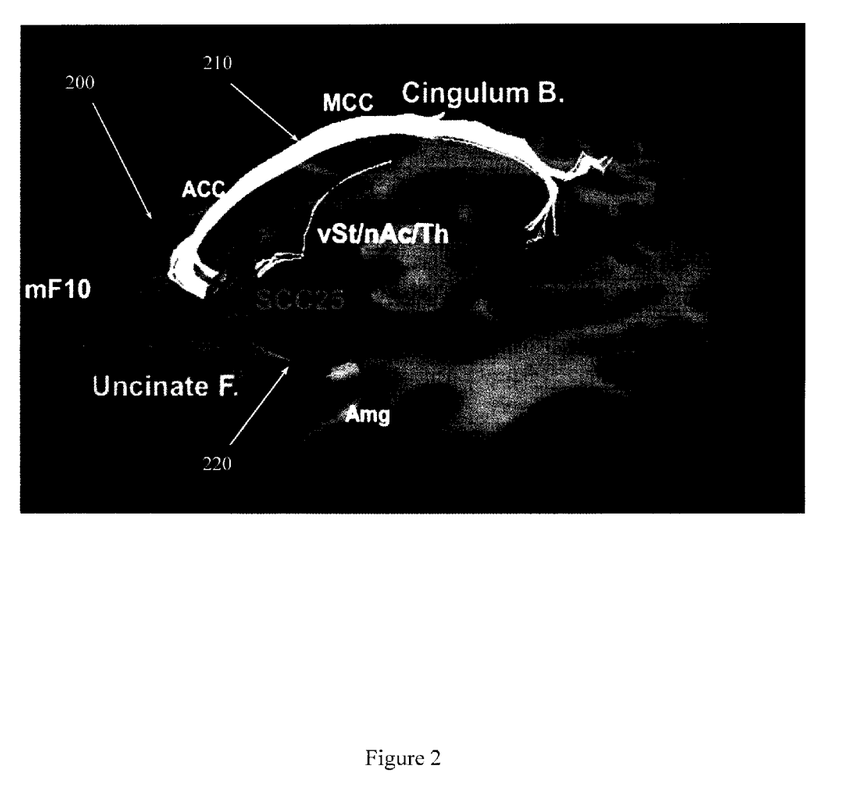
FIG. 2 illustrates three white matter pathways.

FIG. 2 illustrates three white matter pathways that may be activated for SCC DBS for treatment of TRD. Pathway 200 concerns the forceps minor. Pathway 220 concerns the uncinate fasciculus. Pathway 210 concerns the cingulate bundle. mF10 represents the medial frontal Brodmann Area. vSt is the ventral striatum, nAc is the nucleus accumbens, Th is the thalamus, SCC25 is the subcallosal cingulate cortex, Amg is the amygdala, ACC is the anterior cingulate cortex, and MCC is the middle cingulate cortex.

Figure 3:
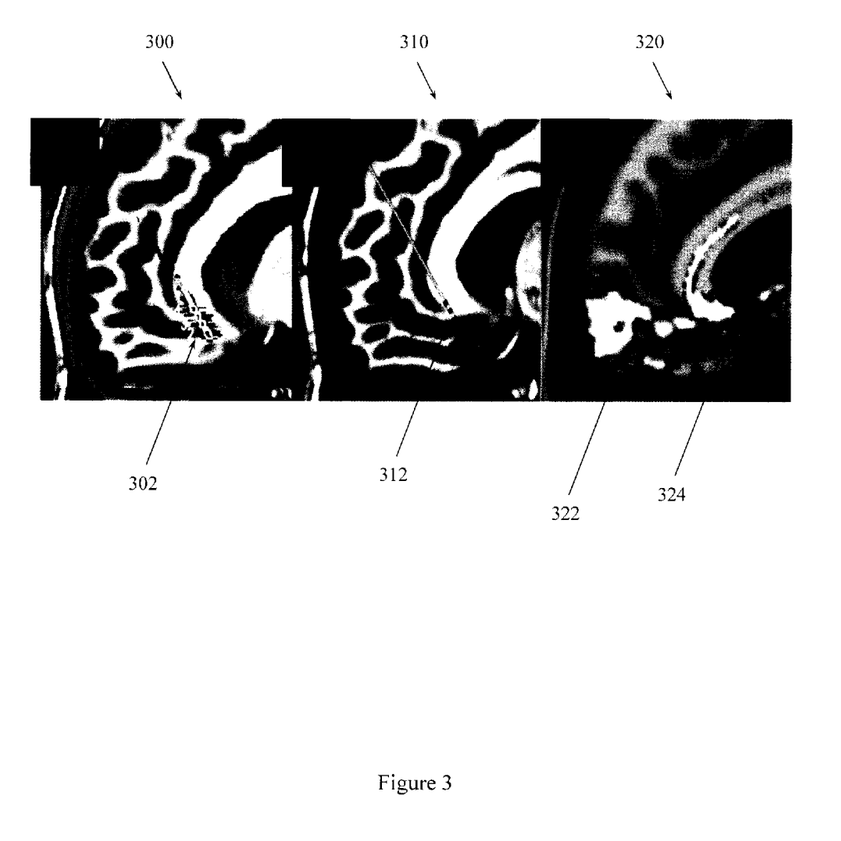
FIG. 3 illustrates a post-surgical computed tomography (CT) image overlapped onto a pre-surgical T1 image, an activation volume, and probabilistic tractography connections from a calculated activation volume.

FIG. 3 presents an image 300 that represents a post-surgical computed tomography (CT) image overlapped onto a pre-surgical T1 image. Electrodes 302 are visible in the patient brain in image 300. FIG. 3 also presents a view 310 of an activation volume using an example contact and typical parameters for a patient (e.g., 130 Hz, 90 us, 6 mA). The activation volume 312 is associated with DBS provided at the electrodes 302. FIG. 3 also presents a view 320 of probabilistic tractography connections from a calculated activation volume. Areas 322 and 324 may be activated by the DBS provided at the electrodes 302.

Figure 4:
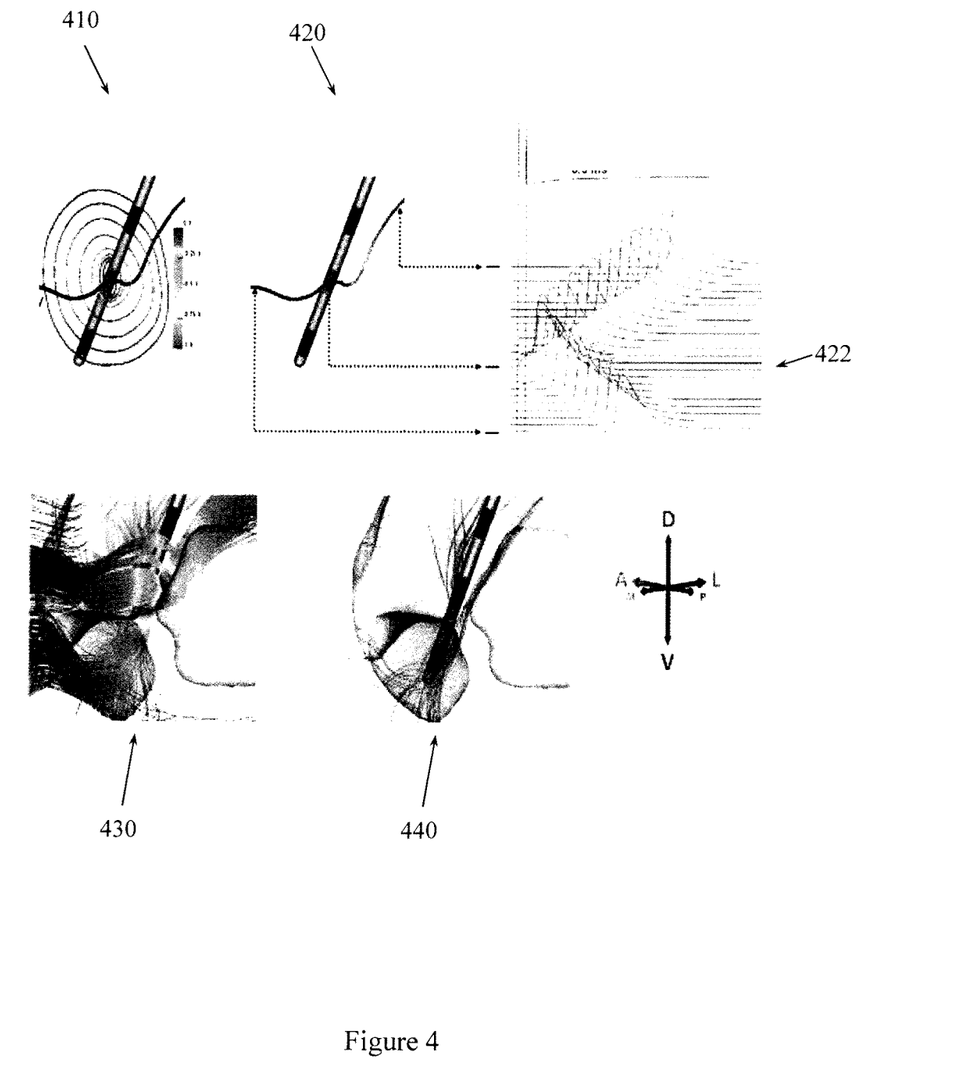
FIG. 4 illustrates information associated with a patient-specific model of axonal activation.

FIG. 4 presents information concerning a patient-specific model of axonal activation. View 410 illustrates an electric field generated by patient-specific stimulation settings represented by iso-potential contours. View 420 illustrates stimulation-induced extracellular potentials (Ve) interpolated onto an axon model. Line 422 corresponds to the highest Ve magnitude. Action potentials initiate in the axon at the node of Ranvier where the second spatial derivative of the extracellular potential is largest. Once initiated, action potentials propagate in both directions along the axon. View 430 illustrates extracellular voltages generated by patient-specific stimulation settings coupled to multi-compartment cable models of axons in the VAIC. View 440 illustrates axon models directly activated by DBS. The data presented in view 440 was generated for a patient using −5V, 90 Is, 130 Hz.

The white matter pathways illustrated in FIG. 2, the activation models illustrated in FIG. 3, and the stimulation information illustrated in FIG. 4 provide the basis for a system for neuro-modulating a distributed multi-region network in a brain. The system may include an apparatus that selects a location for a member of a plurality of DBS electrodes that will activate a combination of white matter pathways associated with the distributed multi-region network. The locations for the member of the plurality of DBS electrodes, and the coverage provided by the entire plurality of DBS electrodes are selected based, at least in part, on a pre-implantation image of the brain and a probabilistic activation model of the distributed multi-region network. The system may include an apparatus that selects an initial stimulation parameter for DBS to be applied through the member of the plurality of DBS electrodes. The initial stimulation parameter may be selected based, at least in part, on a post-implantation image of the brain and the probabilistic activation model of the distributed multi-region network. After implantation, the stimulation parameters may need to be updated. Thus, the system may also include an apparatus that selects a modified stimulation parameter for DBS to be applied through the member of the plurality of DBS electrodes. The modified stimulation parameter may be selected based, at least in part, on the initial stimulation parameter, an LFP measured in the distributed multi-region network in response to DBS applied using the initial stimulation parameter, the probabilistic activation model of the distributed multi-region network, and the post-implantation image of the brain.

Figure 5:
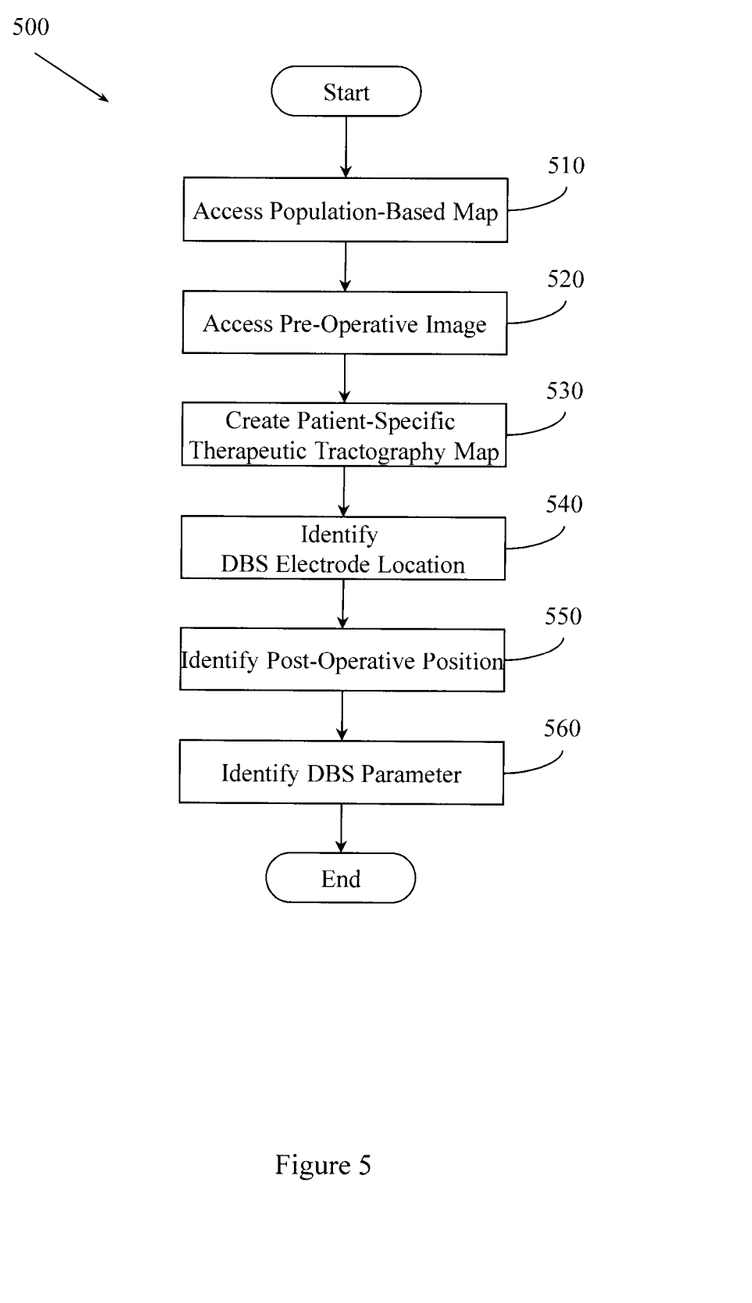
FIG. 5 illustrates a method associated with individualized planning for DBS.

FIG. 5 illustrates a method 500 associated with individualized planning for DBS. Method 500 includes, at 510, accessing a population-based therapeutic tractography map of a human brain. Population-based therapeutic tractography maps are described in provisional applications 61/913,349 and 61/954,638. Accessing the population-based therapeutic tractography map may include, for example, reading electronic data from a computer memory, receiving electronic data from a computer, or other computer-related activity. In one embodiment, the population-based therapeutic tractography map is based on probabilistic tractography including whole-brain analysis and seed-to-target analysis.

Method 500 also includes, at 520, accessing a pre-operative medical image of a brain of a patient. Accessing the pre-operative medical image may include, for example, reading electronic data from a computer memory, receiving electronic data from a computer, or other computer-related activity. In one embodiment, the pre-operative medical image is a diffusion tensor magnetic resonance image. Thus, accessing the pre-operative medical image may include communicating with an MRI apparatus. Pre-operative medical images are described in provisional applications 61/913,349 and 61/954,638.

Method 500 also includes, at 530, creating a patient-specific therapeutic tractography map for the brain of the patient. The patient-specific therapeutic tractography map may be created from, for example, the population-based therapeutic tractography map and the pre-operative medical image. Creating the patient-specific therapeutic tractography map may include manipulating electronic data or other computer based activity. Patient-specific therapeutic tractography maps are described in provisional applications 61/913,349 and 61/954,638.

Method 500 also includes, at 540, identifying a desired location for a DBS electrode in the brain of the patient. The location may be identified based, at least in part, on the patient-specific therapeutic tractography map for the brain of the patient and a desired DBS therapeutic effect. The location may be selected to facilitate activating specific targeted white matter pathways. Identifying the location may include, for example, providing x,y,z co-ordinates or other coordinates in a frame of reference relevant to neuro-surgery, indicating a location on a medical image, or providing other data or indicia.

Method 500 may also include, at 550, identifying an actual postoperative location of the DBS electrode from a post-operative medical image of the brain of the patient. Post-operative medical images are described in provisional applications 61/913,349 and 61/954,638. The actual location of an electrode may be described by x,y,z co-ordinates or other co-ordinates in a frame of reference relevant to neurosurgery, a location on a medical image, or other data or indicia.

Method 500 may also include, at 560, identifying a parameter for a DBS stimulation to be performed to achieve the desired DBS therapeutic effect using the DBS electrode. The parameter may be, for example, voltage, frequency, duration, wave form, or other parameter. The parameter may be identified based on, for example, the actual post-operative location of the DBS electrode, the therapeutic tractography map for the brain of the patient, and the desired therapeutic effect. Identifying the parameter may include changing a value in a computer memory, in a register, in a file, on a display, or elsewhere. The actual post-operative location of a DBS electrode may differ from the planned location due, for example, to issues encountered during surgery.

In different embodiments, the desired DBS therapeutic effect is treatment of depression, treatment of TRD, treatment of obsessive compulsive disorder (OCD), treatment of epilepsy, treatment of Parkinson's disease, or treatment of Alzheimer's disease. When the desired DBS therapeutic effect is treatment of TRD, the desired location for the DBS electrode may be a position that activates a pathway from the bilateral forceps to the medial frontal cortex, a position that activates a pathway from the cingulate bundle to the cingulate cortex, and/or a position that activates a pathway from the descending subcortical midline fibers to the subcortical nuclei. Examples of these pathways are illustrated in FIG. 2. A plurality of electrodes may be placed and stimulation parameters for the plurality of electrodes may be selected to achieve the desired coverage of the combination of pathways.

Figure 6:
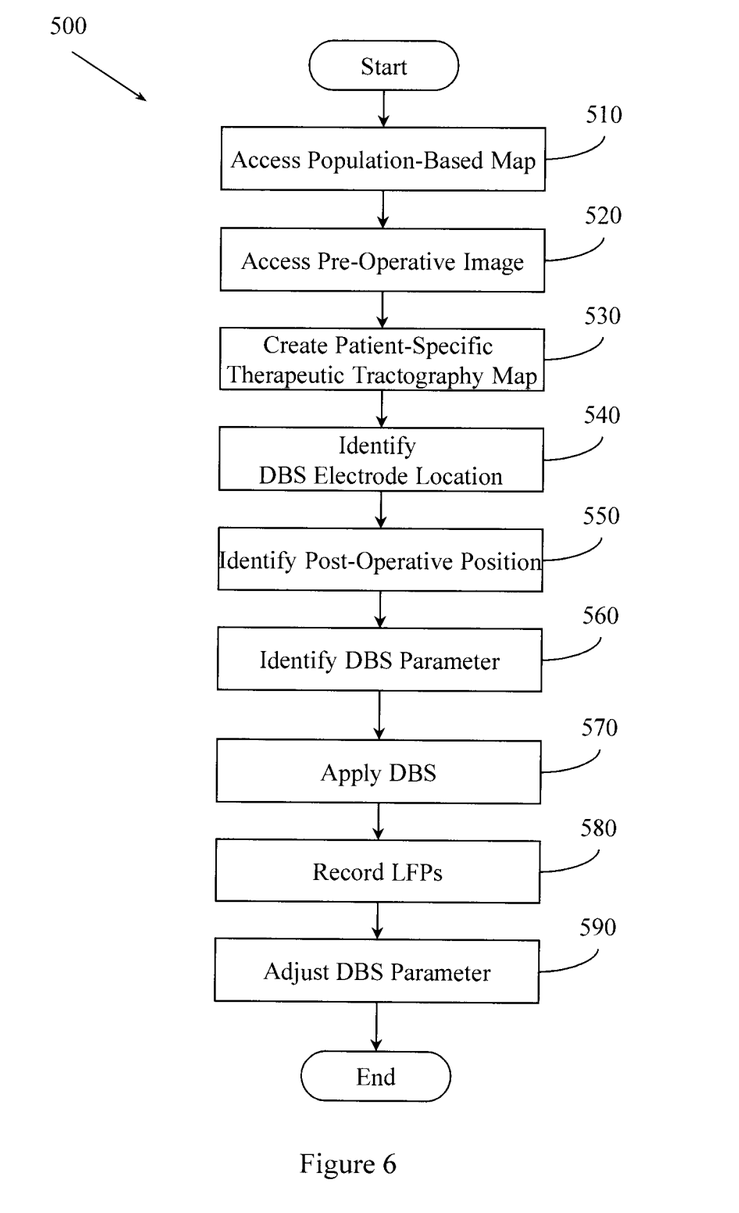
FIG. 6 illustrates a method associated with individualized planning for DBS.

FIG. 6 illustrates another embodiment of method 500. This embodiment also includes, at 570, controlling a DBS apparatus to apply the DBS through the DBS electrode according to the parameter. Controlling the DBS apparatus may include providing an electronic control signal to the DBS apparatus, writing a value to a memory or register in the DBS apparatus, providing a voltage to the DBS apparatus, or other electrical or mechanical operation. Once the DBS has been applied, then the results of the DBS can be measured and a DBS parameter may be selectively modified based on the measurements. Thus, this embodiment of method 500 also includes, at 580, controlling the DBS apparatus to record an LFP at a stimulation site associated with the DBS electrode or at an activation site associated with the desired therapeutic effect. The LFPs may be produced in response to applying the DBS through the DBS electrode according to the parameter. This embodiment of method 500 also includes, at 590, selectively adjusting the parameter based, at least in part, on the LFP recorded at the stimulation site or the LFP recorded at the activation site. For example, if the LFPs recorded at the stimulation site or the target activation site indicate that the target activation site has not been activated, then the DBS parameters may be changed in an attempt to cause activation at the target activation site. However, if the LFPs recorded at the stimulation site or the target activation site indicate that the target activation site has been over activated, then parameters may be adjusted to reduce the activation. In one embodiment, applying the DBS, recording the LFP, and updating the DBS parameter are performed in an ongoing closed loop feedback approach.

Figure 7:
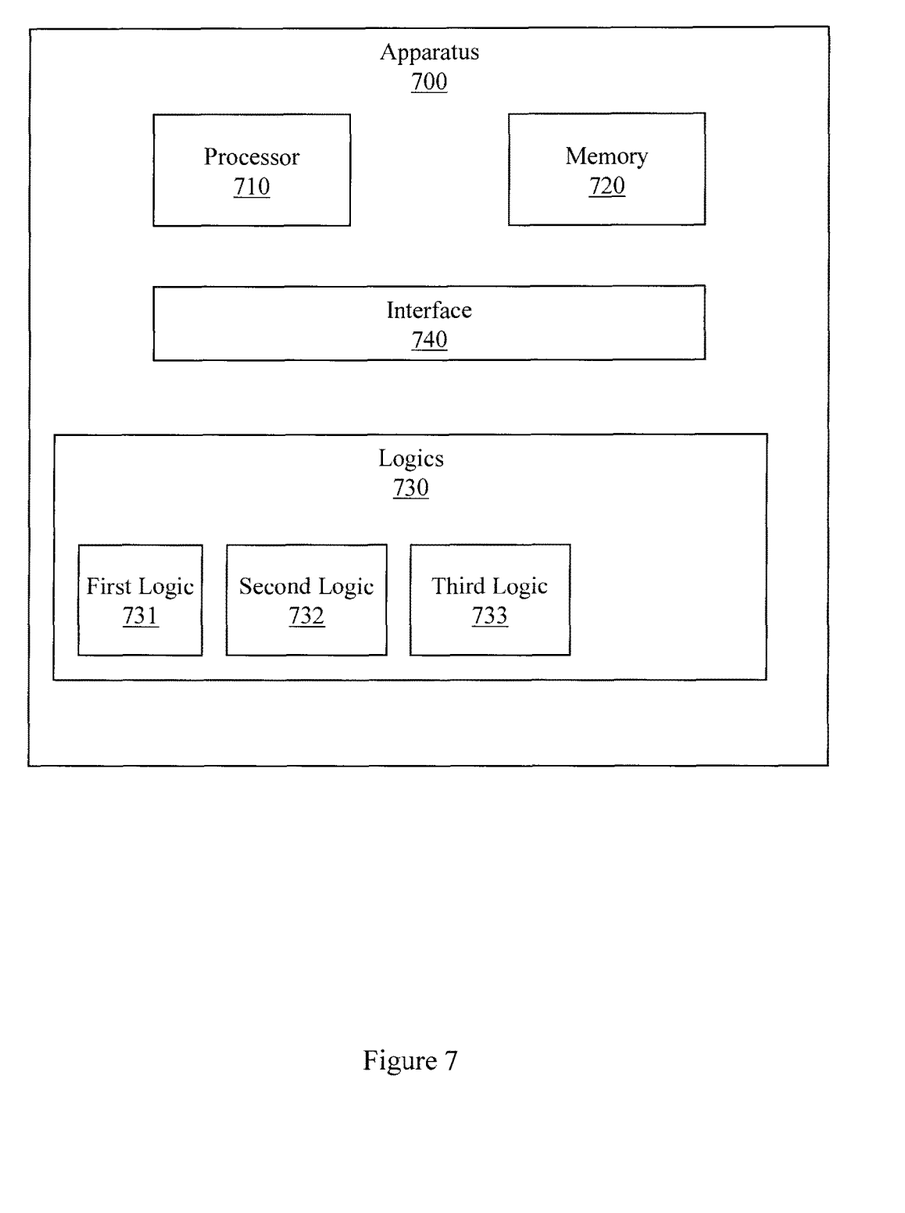
FIG. 7 illustrates an apparatus associated with individualized planning for DBS.

FIG. 7 illustrates an apparatus 700 associated with individualized planning for DBS. Apparatus 700 facilitates controlling patient-specific selective activation of a combination of targeted white matter pathways to treat a neurological condition using DBS. Apparatus 700 may include a processor 710, a memory 720, a set 730 of logics, and an interface 740 that connects the processor 710, the memory 720, and the set 730 of logics. The processor 710 may be, for example, a microprocessor in a computer, a specially designed circuit, a field-programmable gate array (FPGA), an application specific integrated circuit (ASIC), a processor in a mobile device, a system-on-a-chip, a dual or quad processor, or other computer hardware. The memory 720 may store data concerning activation maps, stimulation parameters or recorded LFPs.

Apparatus 700 may interact with other apparatus, processes, and services through, for example, a computer network. Apparatus 700 may be, for example, a computer, a laptop computer, a tablet computer, a personal electronic device, a smart phone, a system-on-a-chip (SoC), or other device that can access and process data.

In one embodiment, the functionality associated with the set of logics 730 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). "Logic", as used herein, may include but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

The set 730 of logics may facilitate individualized planning for DBS. The individualized planning may be activation map based and may be directed at activating a combination of neural pathways. The set 730 of logics may include a first logic 731 that creates a patient-specific therapeutic tractography map of a patient brain. The patient-specific therapeutic tractography map may be built based, at least in part, on a pre-operative medical image of the patient brain and a population-based therapeutic tractography map of the human brain. The population-based therapeutic tractography map of the human brain may in turn be based, at least in part, on activation volume tractography. In one embodiment, the population-based therapeutic tractography map is calculated using probabilistic tractography including whole-brain analysis and seed-to-target analysis. In one embodiment, the pre-operative medical image of the patient brain is an MRI image. The MRI image may be, for example, a diffusion tensor MRI image. In one embodiment, the patient-specific therapeutic tractography map identifies one or more patient-specific stimulation volumes.

The set 730 of logics may also include a second logic 732 that identifies one or more desired DBS electrode placements and one or more stimulation parameters for treatment of the neurological condition using DBS. Some neurological conditions may be treatable using a combination of pathways that can be activated by a single electrode. Other neurological conditions may be treatable using a combination of pathways that can be activated using two or more electrodes. The DBS electrode placements or stimulation parameters may be selected based, at least in part, on the patient-specific therapeutic tractography map. In one embodiment, the DBS electrode placements and the stimulation parameters facilitate activation of axons located in the combination of white matter pathways.

The neurological conditions that can be treated by activating a combination of white matter pathways includes, but is not limited to, depression, TRD, epilepsy, Parkinson's disease, Alzheimer's disease, and OCD. When the neurological condition is TRD, the combination of white matter pathways may include a pathway from the bilateral forceps to the medial frontal cortex, a pathway from the cingulate bundle to the cingulate cortex, or a pathway from the descending subcortical midline fibers to the subcortical nuclei.

The set 730 of logics may also include a third logic 733 that selectively modifies the one or more stimulation parameters. The stimulation parameters may be modified based, at least in part, on actual locations of the one or more DBS electrodes as determined from a post-operative medical image of the patient brain and on the patient-specific therapeutic tractography map. The post-operative medical image of the patient brain may reveal that the electrodes were not placed or do not reside exactly at the planned locations.

Figure 8:
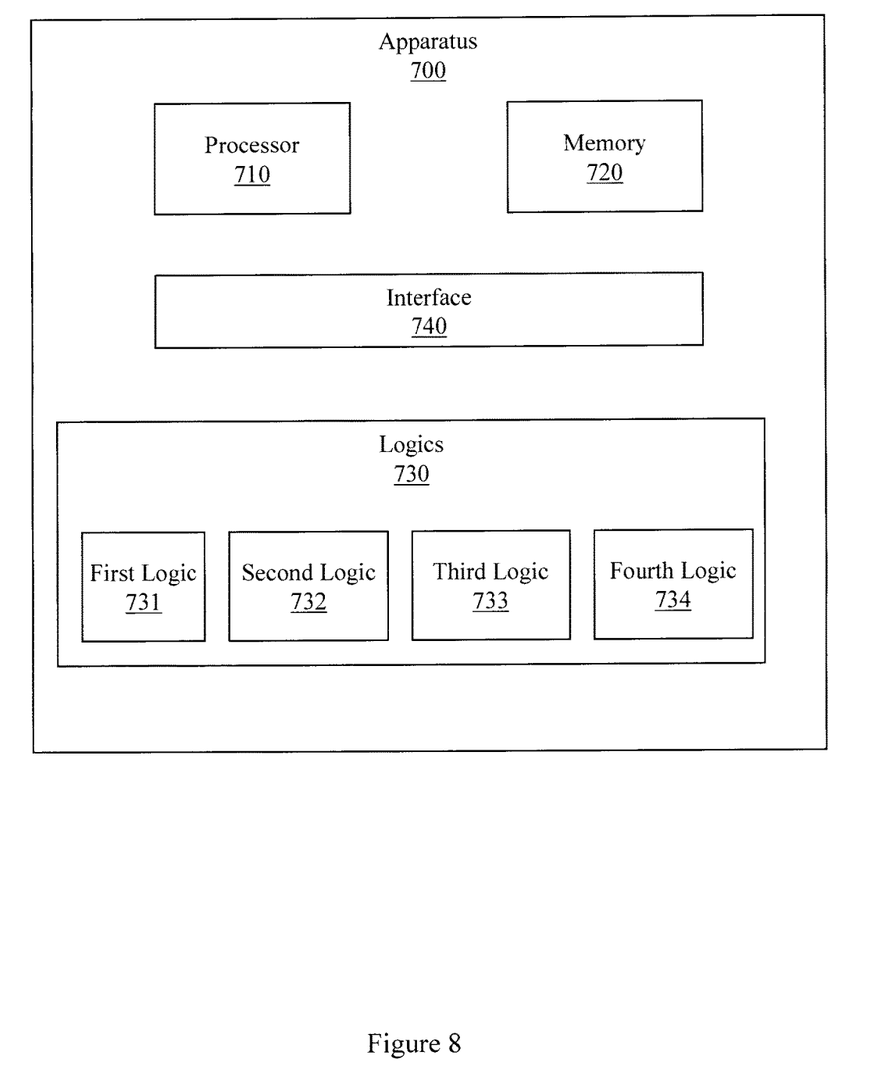
FIG. 8 illustrates an apparatus associated with individualized planning for DBS.

FIG. 8 illustrates another embodiment of apparatus 700. This embodiment includes a fourth logic 734 that selectively modifies the one or more stimulation parameters. The stimulation parameters may be modified based, at least in part, on the actual locations of the one or more DBS electrodes and the patient-specific therapeutic tractography map. The stimulation parameters may also be modified based, at least in part, on signals recorded at a stimulation site associated with the DBS electrodes or on signals recorded at an activation target associated with the DBS electrodes. The signals may be, for example, local field potentials (LFPs) measured using electrophysiological recording.

In one embodiment, the fourth logic 734 may perform closed loop feedback to modify the stimulation parameters in real-time. For example, a clinical DBS system may rely on electrophysiological recordings of LFPs to provide a closed-loop control signal. The recordings could be made at the stimulation site, or at a distant but strategic site elsewhere in the patient brain. For example, in SCC DBS, LFPs could be recorded in the ventral medial prefrontal cortex to verify that the desired activation of forceps minor and/or uncinate fasciculus is occurring. This LFP control signal may then be cross validated with the DBS tractography results in an iterative loop as stimulation parameter settings are adjusted to improve or even maximize therapeutic benefit.

Example apparatus and methods were tested in sixteen patients as described in the provisional applications 61/913,349 and 61/954,638. To summarize the testing, pre-operative high-resolution MRI, including DTI, data were acquired in 16 patients with TRD who then received SCC DBS. Computerized tomography was used post-operatively to locate DBS contacts. The stimulation volume around the active contacts for chronic stimulation was modeled for each patient. Probabilistic tractography was used to delineate the white matter tracts that traveled through the stimulation volume. Patient-specific tract maps were calculated using whole-brain and seed-to-target analyses with regions selected from whole-brain analysis. Clinical evaluations of therapeutic outcome from SCC DBS were defined at 6 months. Whole brain tractography demonstrated that all DBS responders at six months (n=6) shared bilateral pathways from their activation volumes to (1) medial frontal cortex via forceps minor, (2) rostral and dorsal cingulate cortex via the cingulum bundle, and (3) subcortical nuclei. Non-responders did not consistently show these connections. Specific anatomical coordinates of the active contacts did not discriminate responders from non-responders. Thus, patient-specific DBS modeling combined with DTI tractography facilitated identifying a combination of tracts that mediate SCC DBS antidepressant response.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the embodiments described herein. Therefore, the invention is not limited to the specific details, the representative apparatus, and illustrative examples shown and described. Thus, this application is intended to embrace alterations, modifications, and variations that fall within the scope of the appended claims.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

Although the subject matter has been described in language specific to structural features or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus for controlling patient-specific selective activation of a combination of targeted white matter pathways to treat a neurological condition using deep brain stimulation (DBS), comprising:
   a first circuit that creates a patient-specific therapeutic tractography map of a patient brain based, at least in part, on a pre-operative medical image of the patient brain and a population-based therapeutic tractography map of the human brain, where the pre-operative medical image of the patient brain is a diffusion tensor magnetic resonance imaging (MRI) image, where the population-based therapeutic tractography map of the human brain is based, at least in part, on activation volume tractography derived from a neural response to a specific electrical stimulation parameter associated with a neurostimulation;

a second circuit that identifies one or more desired DBS electrode placements and one or more stimulation parameters for treatment of the neurological condition using DBS based, at least in part, on the patient-specific therapeutic tractography map, where the one or more DBS electrode placements and the one or more stimulation parameters facilitate activation of axons located in the combination of white matter pathways; and a third circuit that selectively modifies the one or more stimulation parameters based, at least in part, on actual locations of the one or more DBS electrodes as determined from a post-operative medical image of the patient brain and on the patient-specific therapeutic tractography map.

2. The apparatus of claim 1, where the neurological condition is depression, treatment resistant depression (TRD), epilepsy, Parkinson's disease, Alzheimer's disease, or obsessive compulsive disorder (OCD).

3. The apparatus of claim 1, where the neurological condition is treatment resistant depression (TRD) and the combination of white matter pathways includes a pathway from the bilateral forceps to the medial frontal cortex, a pathway from the cingulate bundle to the cingulate cortex, or a pathway from the descending subcortical midline fibers to the subcortical nuclei.

4. The apparatus of claim 1, where the neurological condition is treatment resistant depression (TRD) and the combination of white matter pathways includes a pathway from the bilateral forceps to the medial frontal cortex, a pathway from the cingulate bundle to the cingulate cortex, and a pathway from the descending subcortical midline fibers to the subcortical nuclei.

5. The apparatus of claim 1, where the population-based therapeutic tractography map is calculated using probabilistic tractography including whole-brain analysis and seed-to-target analysis.

6. The apparatus of claim 1, where the patient-specific therapeutic tractography map identifies one or more patient-specific stimulation volumes.

7. The apparatus of claim 1, comprising a fourth circuit that selectively modifies the one or more stimulation parameters based, at least in part, on the actual locations of the one or more DBS electrodes, the patient-specific therapeutic tractography map, and one or more signals recorded at a stimulation site associated with the one or more DBS electrodes or at an activation target associated with the one or more DBS electrodes, where the one or more signals are local field potentials (LFPs) measured using electrophysiological recording.

8. The apparatus of claim 1, where the neurological condition is dystonia.

9. The apparatus of claim 8, where the combination of targeted white matter pathways includes dopaminergic connections in a nigropallidal pathway from the substantia nigra to the globus pallidus.

10. The apparatus of claim 8, where the combination of targeted white matter pathways includes dopaminergic connections in a nigropallidal pathway from the pars compacta subregion of the substantia nigra to the pars interna subregion of the globus pallidus.

11. The apparatus of claim 8, where the combination of targeted white matter pathways includes glutaminergic connections in a subthalamopallidal pathway from the subthalamic nucleus to the globus pallidus.

12. The apparatus of claim 8, where the combination of targeted white matter pathways includes glutaminergic connections in a subthalamopallidal pathway from the subthalamic nucleus pars compacta to the globus pallidus pars externa.

13. The apparatus of claim 8, where the combination of targeted white matter pathways includes GABA-ergic projections in a pallidothalamic pathway from the pars externa of the globus pallidus or the pars interna of the globus pallidus to thalamic subnuclei including the lateral posterior nucleus, the ventral oral nucleus, the centro-media parafascicular complex, the ventral lateral nucleus, or the ventral anterior nucleus.

14. The apparatus of claim 13, where the pallidothalamic pathway includes the ansa lenticularis fiber tract or the lenticular fasciculus fiber tract.

15. The apparatus of claim 8, where the combination of targeted white matter pathways includes projections in a stiatopallidal pathway from the caudate striatum or the putamen striatum to the globus pallidus.

16. The apparatus of claim 8, where the combination of targeted white matter pathways includes cortical projections in a cortico-pallidal pathway to the globus pallidus from one or more cortical regions.

17. The apparatus of claim 16, where the one or more cortical regions include a premotor region, a motor region, a supplementary motor region, a posterior parietal region, or a sensory region.

18. The apparatus of claim 8, where the combination of targeted white matter pathways include a cerebello-pallidal pathway, a pallido-parapontine pathway, or a pallido-retrorubral area pathway.

19. The apparatus of claim 8, where the combination of targeted white matter pathways include a hyperdirect pathway from the cortical motor M1 region to the subthalmic nucleus.

* * * * *